United States Patent
Treister

(10) Patent No.: US 9,279,270 B1
(45) Date of Patent: Mar. 8, 2016

(54) SYSTEM FOR AFFIXING A BLANKET TO GROUND

(71) Applicant: John Christian Treister, Placentia, CA (US)

(72) Inventor: John Christian Treister, Placentia, CA (US)

( * ) Notice: Subject to any disclaimer, the term of this patent is extended or adjusted under 35 U.S.C. 154(b) by 0 days.

(21) Appl. No.: 14/591,571

(22) Filed: Jan. 7, 2015

Related U.S. Application Data

(60) Provisional application No. 61/925,084, filed on Jan. 8, 2014.

(51) Int. Cl.
*A47G 9/06* (2006.01)
*A47G 9/04* (2006.01)
*E04H 15/62* (2006.01)

(52) U.S. Cl.
CPC ............. *E04H 15/62* (2013.01); *A47G 9/062* (2013.01); *A47G 9/06* (2013.01)

(58) Field of Classification Search
CPC ............ A47G 9/06; A47G 9/062; A47G 9/04
USPC .............................. 52/2.25, 4, 3, 23; 135/118
See application file for complete search history.

(56) References Cited

U.S. PATENT DOCUMENTS

| | | | | |
|---|---|---|---|---|
| 1,560,114 A * | 11/1925 | Skog | ................ | E04H 15/18 135/117 |
| 1,871,570 A * | 8/1932 | Weber | ................ | 52/3 |
| 2,188,747 A * | 1/1940 | Bittick | ................ | E04H 15/006 135/117 |
| 2,939,468 A * | 6/1960 | Boyce | ................ | E04H 15/62 135/118 |
| 3,763,907 A * | 10/1973 | Hockley et al. | ................ | 150/154 |
| 4,567,696 A * | 2/1986 | Malet | ................ | 52/2.25 |
| 4,682,447 A * | 7/1987 | Osborn | ................ | 52/3 |
| 4,862,638 A * | 9/1989 | Stevenson | ................ | 43/114 |
| 5,018,229 A * | 5/1991 | Eberhart | ................ | A47G 9/062 428/100 |
| 5,406,659 A * | 4/1995 | Camp | ................ | 5/417 |
| 5,608,992 A * | 3/1997 | Floyd | ................ | 52/3 |
| 5,713,383 A * | 2/1998 | Ramirez | ................ | E04H 15/62 135/118 |
| 5,862,876 A * | 1/1999 | Gordon et al. | ................ | 180/268 |
| 6,176,050 B1 * | 1/2001 | Gower | ................ | 52/222 |
| 6,224,139 B1 * | 5/2001 | Weyand | ................ | 296/100.16 |
| 6,226,813 B1 * | 5/2001 | Wilburn | ................ | A47G 9/062 135/118 |
| 6,474,022 B1 * | 11/2002 | Double et al. | ................ | 52/3 |
| 6,571,815 B1 * | 6/2003 | Hill | ................ | 135/96 |
| 6,865,852 B2 * | 3/2005 | Gower | ................ | 52/222 |
| 7,392,620 B1 * | 7/2008 | Watson, Jr. | ................ | 52/4 |
| 8,122,538 B2 * | 2/2012 | McBrearty | ................ | A47G 9/062 297/219.1 |
| D688,900 S * | 9/2013 | McBrearty | ................ | D6/608 |
| 8,857,128 B2 * | 10/2014 | Kenney | ................ | 52/656.1 |
| 2012/0090249 A1 * | 4/2012 | Schor et al. | ................ | 52/4 |

* cited by examiner

*Primary Examiner* — Phi A

(74) *Attorney, Agent, or Firm* — Plager Schack LLP

(57) ABSTRACT

A system for affixing a blanket to ground includes at least one corner flap mechanically coupled to the blanket and configured with a removable edge with the blanket. At least one stake is mechanically coupled to the blanket. The at least one stake is configured to be removed from underneath the at least one corner flap and into the ground.

8 Claims, 3 Drawing Sheets

SYSTEM FOR AFFIXING A BLANKET TO GROUND

RELATED APPLICATION

This application claims priority to provisional patent application U.S. Ser. No. 61/925,084 filed on Jan. 8, 2014, the entire contents of which is herein incorporated by reference.

BACKGROUND

The embodiments herein relate generally to outdoor recreation. More specifically, embodiments of the disclosed invention relate to systems that can be configured to affix a blanket to ground.

Prior to embodiments of the disclosed invention, when laid out, a picnic blanket could be blown around, or displaced by movement on top of the blanket. Embodiments of the disclosed invention solve this problem.

SUMMARY

A system for affixing a blanket to ground includes at least one corner flap mechanically coupled to the blanket and configured with a removable edge with the blanket. At least one stake is mechanically coupled to the blanket. The at least one stake is configured to be removed from underneath the at least one corner flap and into the ground.

In some embodiments, the at least one stake can be attached to a clip string. The clip string can be attached to a clip. The clip can be attached to a grommet string. The grommet string can be attached to a grommet. The grommet can be attached to the blanket.

In some embodiments, the at least one corner flap can be four corner flaps. The at least one stake can be four stakes

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
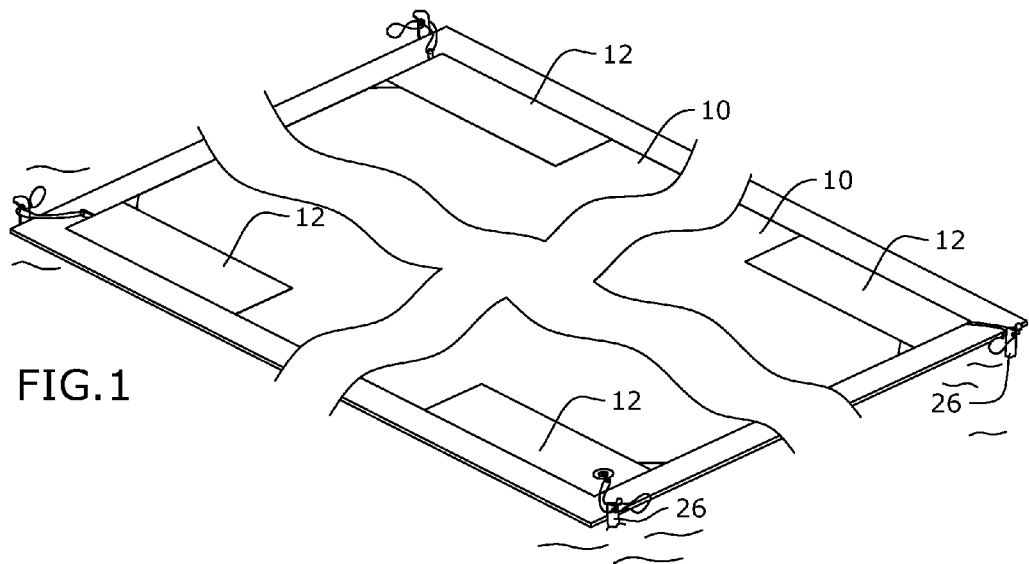
FIG. 1 is a perspective view of the invention shown in use (broken view indicative of indefinite length/width for blanket).
Figure 2:
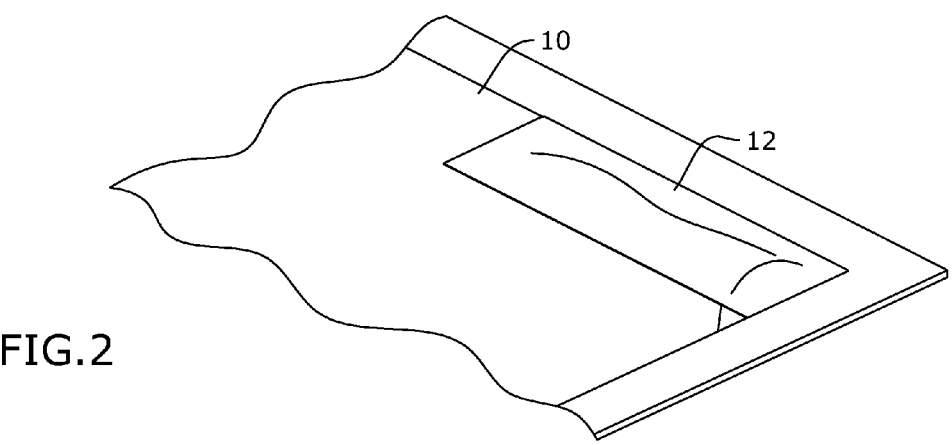
FIG. 2 is a detail perspective view of the invention (single corner) demonstrated with stake in a stowed configuration and flap in a closed position.

By way of example, and referring to FIG. 1 and FIG. 2, blanket 10 is formed in a rectangle having four corners. Each corner is mechanically coupled to a corner flap 12.

Figure 3:
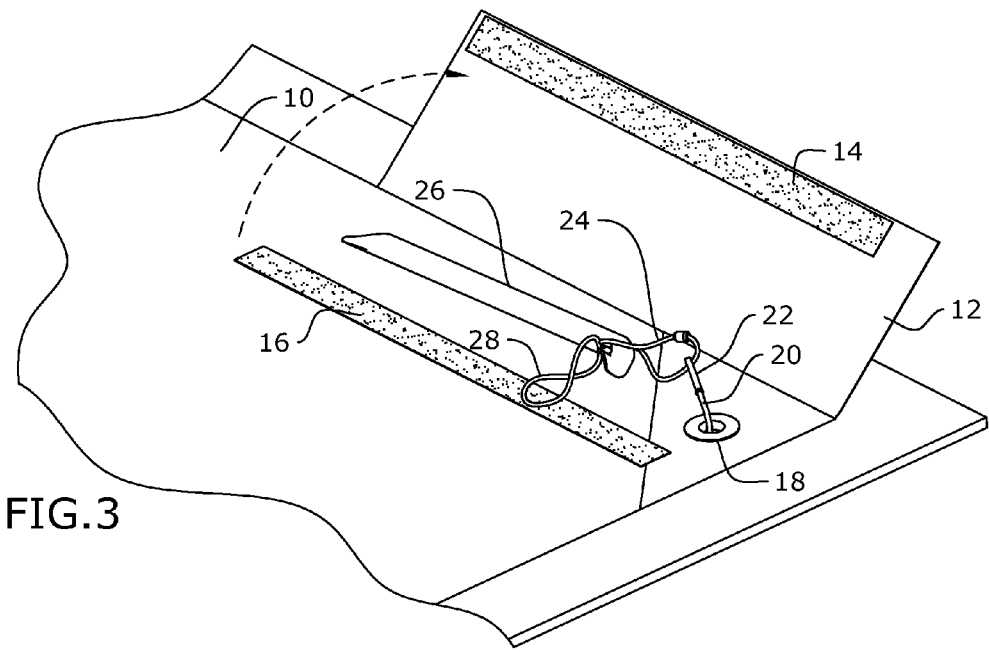
FIG. 3 is a detail perspective view of the invention (single corner) demonstrated with stake in a stowed configuration and flap in an open position.
Figure 4:
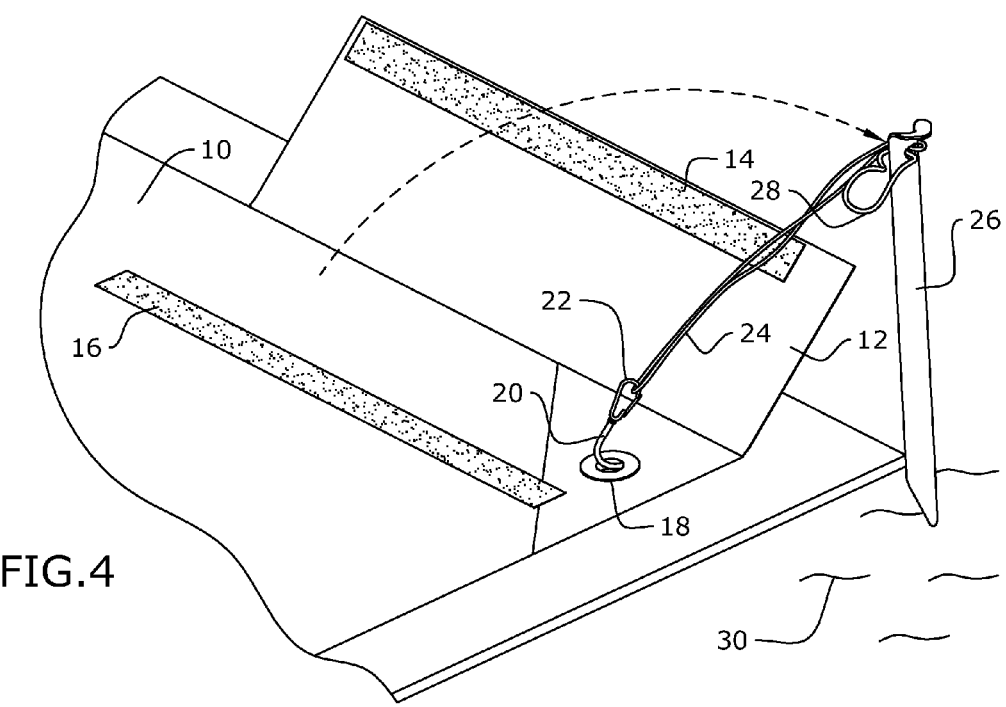
FIG. 4 is a detail perspective view of the invention (single corner) demonstrated with stake in a deployed configuration and flap in an open position.
Figure 5:
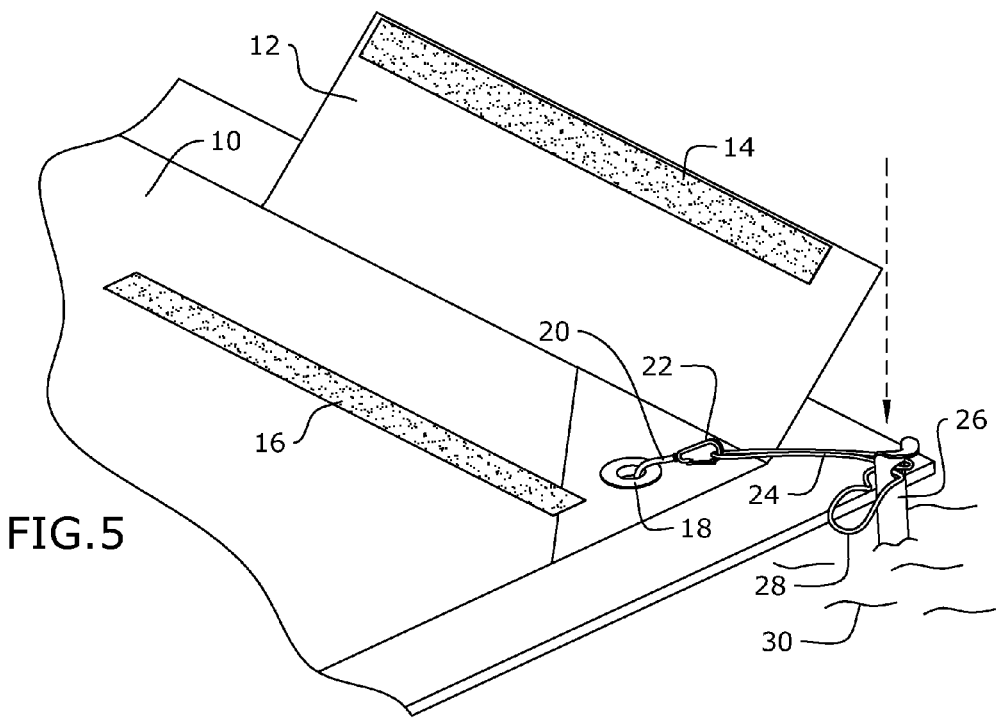
FIG. 5 is a detail perspective view of the invention (single corner) demonstrated with stake in a deployed configuration into ground and flap in an open position.
Figure 6:
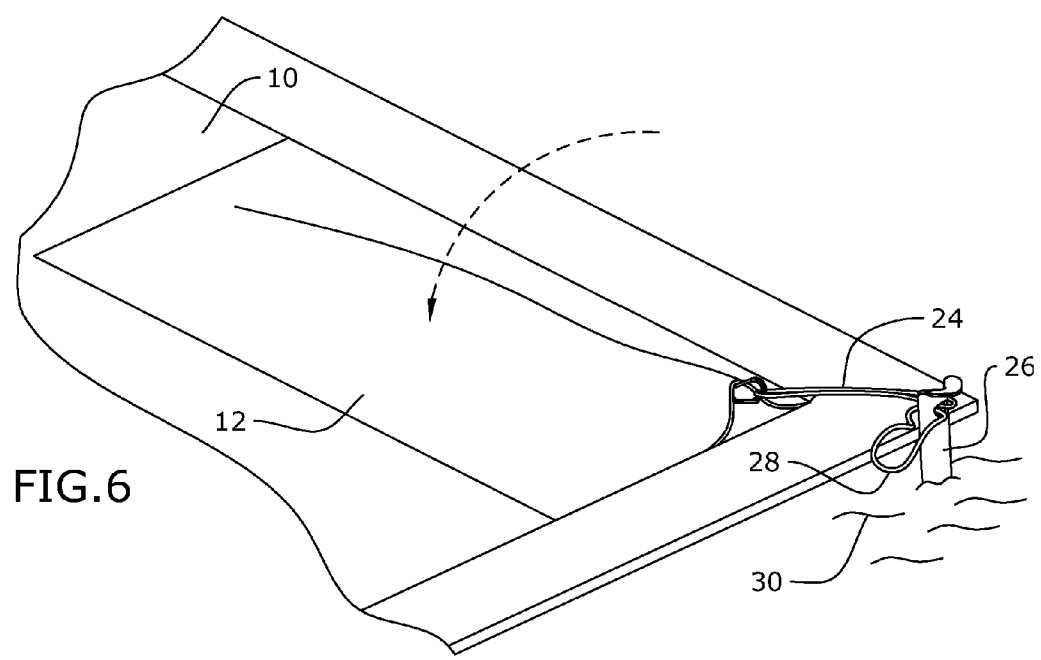
FIG. 6 is a detail perspective view of the invention (single corner) demonstrated with stake in a deployed configuration into ground and flap in a closed position.

As shown in FIG. 3 and FIG. 4, corner flap 12 is mechanically coupled to flap hook and loop fastener 14. Blanket hook and loop fastener 16 is mechanically coupled to blanket 10. In some embodiments it is advantageous to have flap hook and loop fastener 14 on a distal edge of corner flap 12 which is away from an outer edge of blanket 10. This forms a removable edge.

Blanket 10 is mechanically coupled to grommet 18. Grommet 18 is mechanically coupled to grommet string 20. Grommet string 20 is mechanically coupled to clip 22. Clip 22 is mechanically coupled to clip string 24. Clip string 24 is mechanically coupled to stake 26. Stake 26 is mechanically coupled to retractor string 28. Stake 26 is configured to be driven into ground 30.

As shown in FIGS. 3-6, to use the system, the following steps may be used. First, opening corner flap 12 from blanket 10 by detaching flap hook and loop fastener 14 from blanket hook and loop fastener 16. Next, moving stake 26 away from blanket 10. After that, inserting stake 26 into ground 30. Finally, closing corner flap 12 onto blanket 10.

FIGS. 3-6 show at least one corner flap 12 and at least one stake 26, but as shown in FIG. 1, as many as four corner flaps 12 can be used with four stakes 26. Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A system for affixing a blanket to ground; the system comprising:
    a blanket having a distal edge surrounding at least one recess;
    at least one corner flap pivotally attached to the blanket on the distal edge within the at least one recess flush with the distal edge of the blanket; the at least one corner flap having a first edge joined to a second edge and a third edge; a fourth edge, joined to the second edge and the third edge, arranged into a parallelepiped; the first edge attached to the blanket;
    a hook fastener, attached to the fourth edge;
    a loop fastener, attached to the blanket; wherein joining the hook fastener and the loop fastener forms a pocket between the first edge, the second edge, the third edge and the fourth edge;
    at least one stake, mechanically coupled to the blanket, and housed entirely in the pocket in a first mode of operation wherein the at least one corner flap is flush with the distal edge of the blanket;
    wherein a second mode of operation, the at least one stake extends outside of the pocket and horizontal and vertical distal edges of the blanket; wherein the at least one stake is configured to be removed from underneath the at least one corner flap and into the ground perpendicular to the horizontal and vertical distal edges of the blanket.

2. The system of claim 1, wherein the pocket further comprises the at least one corner flap being rectangular in shape with a longer side proximate the distal edge; wherein the longer side is sewn to the blanket such that folding the flap distant the distal edge creates a closed pocket for the first mode of operation; and the at least one stake is attached to a clip string.

3. The system of claim 2, wherein the clip string is attached to a clip.

4. The system of claim 3, wherein the clip is attached to a grommet string.

5. The system of claim 4, wherein the grommet string is attached to a grommet.

6. The system of claim 5, wherein the grommet is attached to the blanket.

7. The system of claim 1, wherein the at least one corner flap is four corner flaps.

8. The system of claim 7, wherein the at least one stake is four stakes.

\* \* \* \* \*